US009226818B2

(12) United States Patent
Campin et al.

(10) Patent No.: US 9,226,818 B2
(45) Date of Patent: Jan. 5, 2016

(54) SENSORS FOR TRIGGERING ELECTRO-ACTIVE OPHTHALMIC LENSES

(71) Applicant: NOVARTIS AG, Basel (CH)

(72) Inventors: John Alfred Campin, Southlake, TX (US); George H. Pettit, Fort Worth, TX (US)

(73) Assignee: NOVARTIS AG, Basel (CH)

( * ) Notice: Subject to any disclaimer, the term of this patent is extended or adjusted under 35 U.S.C. 154(b) by 73 days.

(21) Appl. No.: 14/041,312

(22) Filed: Sep. 30, 2013

(65) Prior Publication Data

US 2014/0156000 A1 Jun. 5, 2014

Related U.S. Application Data

(60) Provisional application No. 61/731,999, filed on Nov. 30, 2012.

(51) Int. Cl.
| | |
|---|---|
| *A61F 2/16* | (2006.01) |
| *G02C 7/00* | (2006.01) |
| *G02C 7/04* | (2006.01) |
| *A61B 5/0488* | (2006.01) |
| *A61B 5/00* | (2006.01) |
| *G02C 7/08* | (2006.01) |
| *A61B 3/09* | (2006.01) |

(52) U.S. Cl.
CPC .............. *A61F 2/1624* (2013.01); *A61B 5/0488* (2013.01); *A61B 5/6803* (2013.01); *G02C 7/04* (2013.01); *G02C 7/083* (2013.01); *A61B 3/09* (2013.01)

(58) Field of Classification Search
None
See application file for complete search history.

(56) References Cited

U.S. PATENT DOCUMENTS

| | | | |
|---|---|---|---|
| 4,373,218 A | 2/1983 | Schachar | |
| 6,163,281 A | 12/2000 | Torch | |
| 7,252,006 B2 | 8/2007 | Tai et al. | |
| 8,034,106 B2 * | 10/2011 | Mentak et al. | 623/6.13 |
| 8,149,377 B2 | 4/2012 | Presniakov et al. | |
| 8,574,295 B2 * | 11/2013 | Roholt | 623/6.22 |

(Continued)

FOREIGN PATENT DOCUMENTS

| | | |
|---|---|---|
| WO | 2011163080 A1 | 12/2011 |
| WO | 2012006691 A1 | 1/2012 |

OTHER PUBLICATIONS

PCT/US2013/62594; International Search Report, International Searching Authority, Dec. 12, 2013, 2pgs.

(Continued)

*Primary Examiner* — David H Willse
*Assistant Examiner* — Javier Blanco
(74) *Attorney, Agent, or Firm* — Jason Finch

(57) ABSTRACT

An electro-active ophthalmic lens includes an electromyography sensor, a processor, and an electro-active optical element. The electromyography sensor is configured to detect an electric field in a ciliary muscle of the eye that is proportional to a force exerted by the ciliary muscle and to generate a sensor signal indicative of the electric field. The processor is operable to receive the signal from the electromyography sensor and to determine, based on the sensor signal, an adjustment to optical power for an electro-active optical element and to generate a control signal for the electro-active optical element. The electro-active optical element is operable to receive the control signal and to change an optical power of the electro-active optical element in response to the control signal.

6 Claims, 3 Drawing Sheets

(56) References Cited

U.S. PATENT DOCUMENTS

| | | | |
|---|---|---|---|
| 8,608,310 B2* | 12/2013 | Otis | A61B 5/1486 351/159.03 |
| 9,001,282 B2* | 4/2015 | Archambeau | G02B 3/14 349/13 |
| 2004/0027536 A1 | 2/2004 | Blum et al. | |
| 2005/0049647 A1 | 3/2005 | Olson | |
| 2006/0122530 A1* | 6/2006 | Goodall et al. | 600/546 |
| 2008/0271784 A1 | 11/2008 | Duston et al. | |
| 2009/0163801 A1 | 6/2009 | Sliwa | |
| 2010/0004741 A1* | 1/2010 | Gupta | A61F 2/1627 623/6.22 |

OTHER PUBLICATIONS

PCT/US2013/62594;Written Opinion, International Searching Authority, Dec. 12, 2013, 6pgs.

* cited by examiner

SENSORS FOR TRIGGERING ELECTRO-ACTIVE OPHTHALMIC LENSES

This application claims the priority of U.S. Provisional Patent Application No. 61/731,999 filed on Nov. 30, 2012.

TECHNICAL FIELD

This invention relates generally to the field of ophthalmic lenses and, more particularly, to electro-active ophthalmic lenses.

BACKGROUND OF THE INVENTION

The human eye in its simplest terms functions to provide vision by transmitting light through a clear outer portion called the cornea, and focusing the image by way of a crystalline lens onto a retina. The quality of the focused image depends on many factors including the size and shape of the eye, and the transparency of the cornea and the lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, an opening is made in the anterior capsule and a thin phacoemulsification cutting tip is inserted into the diseased lens and ultrasonically vibrated. The vibrating cutting tip liquifies or emulsifies the lens so that the lens may be aspirated out of the eye. The diseased lens, once removed, is replaced by an IOL.

In the natural lens, distance and near vision is provided by a mechanism known as accommodation. The natural lens is contained within the capsular bag and is soft early in life. The bag is suspended from the ciliary muscle by the zonules. Relaxation of the ciliary muscle tightens the zonules, and stretches the capsular bag. As a result, the natural lens tends to flatten. Tightening of the ciliary muscle relaxes the tension on the zonules, allowing the capsular bag and the natural lens to assume a more rounded shape. In this way, the natural lens can focus alternatively on near and far objects.

As the lens ages, it becomes harder and is less able to change its shape in reaction to the tightening of the ciliary muscle. Furthermore, the ciliary muscle loses flexibility and range of motion. This makes it harder for the lens to focus on near objects, a medical condition known as presbyopia. Presbyopia affects nearly all adults upon reaching the age of 45 to 50. Accordingly, there exists a need for better solutions to the problem of accommodation in IOLs. Additionally, patients may also suffer from other conditions, such as age-related macular degeneration (AMD), which may require an even greater degree of magnification to be able to perform visual functions such as reading.

One approach to providing presbyopia correction is the use of an electro-active optical element in an ophthalmic lens, such as an IOL. The electro-active element has an adjustable optical power based on electrical signals controlling the element, so that the power of the lens can be adjusted based on accommodation demand. An electro-active IOL can include control circuitry, power supplies and wireless communication capabilities, and the componentry can be packaged in a biocompatible material and/or sealed electronic packaging. As yet, however, there has not been a particular sensing approach that has been demonstrated as being sufficiently reliable for functional utility.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

Figure 1:
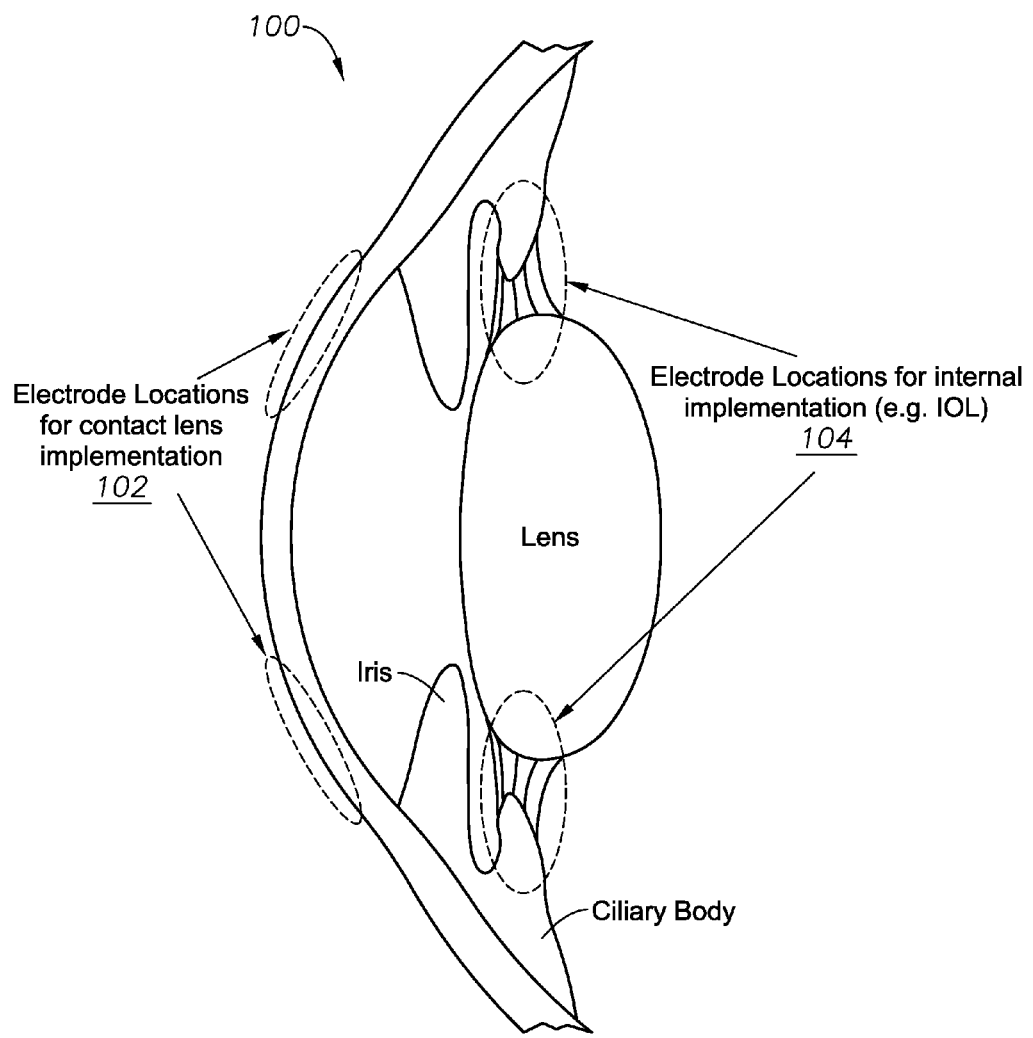
FIG. 1 illustrates the placement in an eye of electromyography sensors corresponding to the locations of a contact lens and an IOL, according to certain embodiments of the present disclosure.

The skilled person in the art will understand that the drawings, described below, are for illustration purposes only. The drawings are not intended to limit the scope of the applicants' disclosure in any way.

DETAILED DESCRIPTION

Various embodiments of the present invention provide sensors for controlling electro-active ophthalmic lenses. In particular embodiments, the sensor provides for automatic control of an electro-active lens. In other embodiments, the sensor provides a user-controlled interface for operating the electro-active lens. While the following description focuses primarily on intraocular lenses, the described techniques could also be used in contact lenses or even spectacles. The embodiments discussed below are exemplary, and various changes can be made to these illustrative embodiments without deviating from the scope of the invention. For example, the features of one embodiment can be combined with those of another embodiment.

One sensing technique that has been relatively successful in muscle activity is the use of electromyography. Electromyography is a technique in which the electric field pattern surrounding the muscle is measured over time (such as by electric potential measurements) to determine the degree of muscle contraction. As contrasted with methods such as calcium channel ion detection or other direct detection of the neural signal, electromyography focuses on the electrical activity of the muscle itself, and as such, has proved to be a more reliable gauge of muscle activity. Furthermore, it can provide a continuous indication of the degree of muscle activity, and particularly the degree of force exerted by the muscle, rather than binary detection of a neurological signal.

Movement of a muscle fiber is triggered by depolarization of within the muscle fiber, accompanied by movement of ions, which produces a change in electric field. As the depolarization propagates down the muscle fiber, a biphasic electric field signal is produced that switches signs from positive to negative as the depolarization wave moves along the fiber. Electromyography sensors detect this change in electric field, which allows the muscle activity to be measured. Measurements in skeletal muscle have demonstrated that the intensity varies monotonically and generally linearly with the force exerted by the muscle, so that the electric field can be used as an indicator of the amount of force exerted by the muscle.

In application to IOLs, the correlation between accommodative demand, the degree to which muscle activity is demanded in response to visual stimuli, and the amount of electrical field in the muscles can be observed in order to calibrate the lens. Despite the later ineffectiveness of accommodation due to hardening of the lens and aging of the ciliary muscle and surrounding connective tissue, the ciliary muscle continues to contract even in presbyopic eyes. This potentially provides an indication of accommodative demand that allows more granular detection than previous sensing techniques, such as detection of neural activity or gross detection of electrical activity as a trigger for accommodation. Consequently, rather than detecting a binary transition between near and far vision, such a system could allow a continuous range of adjustment correlated to the electrical activity of the ciliary muscle tissue, which can in turn be calibrated based on the observed accommodation demand. Such calibration could be based on an average response in the population; alternatively, the calibration could be patient-specific.

FIG. 1 illustrates the placement in an eye 100 of electromyography sensors 102 and 104, corresponding respectively to the locations of a contact lens and an IOL. Electromyography sensors 102 and 104 may represent any suitable form of electrode or detector for measurement of the electric field indicative of the degree of muscle activity in the ciliary muscle 106. In the case of sensors 104 contacting the ciliary muscle, contacts such as fine wires inserted into the muscle fiber or electrode pads touching the muscle may be useful. Where the sensors are not in contact with the ciliary muscle, such as with sensors 102, the sensors 102 may include antennae or other structures that undergo physical or electrical changes in response to changes in electric fields. Multiple sensors 102 and 104 may be placed at different locations with respect to the ciliary muscle. Sensors 102 and 104 may also include one or more reference sensors that provide a reference electric potential. Reference values and differential approaches may be used to increase relative signal strength and/or to improve signal-to-noise ratio.

Figure 2:
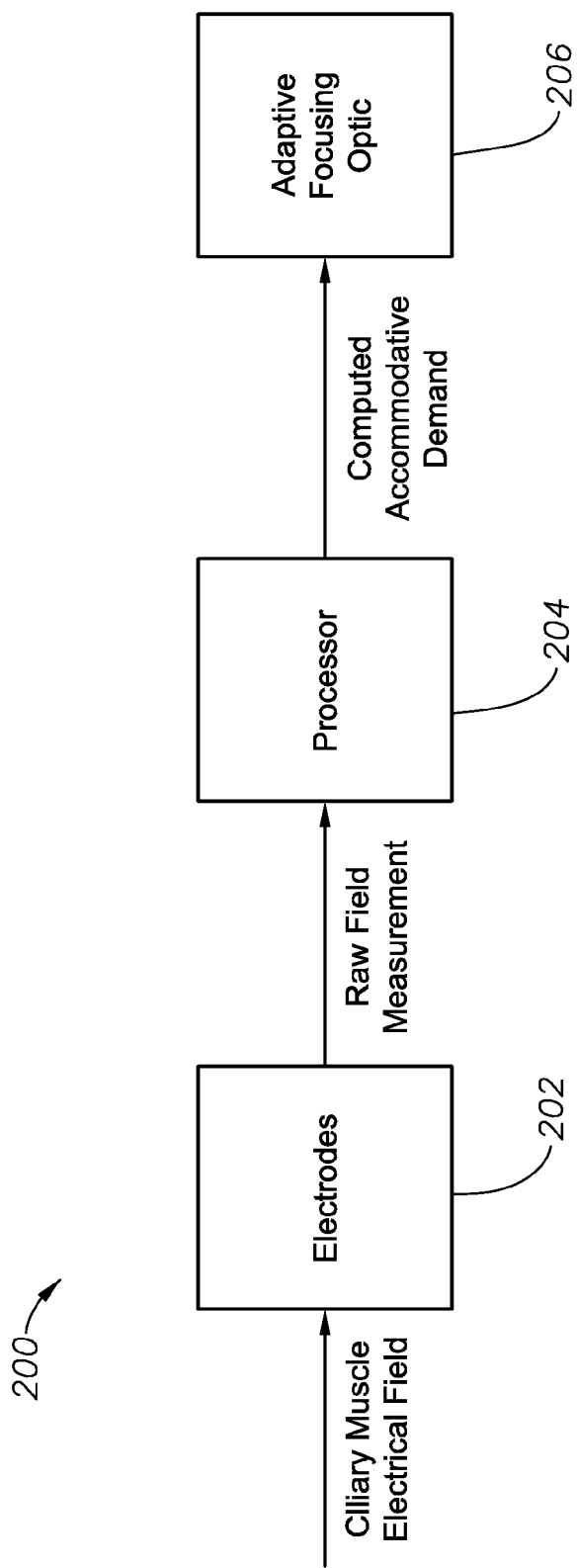
FIG. 2 is a block diagram illustrating the subsystems of an electro-active ophthalmic lens, according to certain embodiments of the present disclosure.

FIG. 2 is a block diagram illustrating the subsystems of an electro-active ophthalmic lens 200 according to particular embodiments of the present invention. Sensors 202 are electromyography sensors such as the sensors 102 and 104 described previously. Because the detected electric field is relatively small (in the range of $10^{-4}$-$10^{-3}$ V), amplification may be used to augment the electrical signal. Processor 204 represents any suitable electronic component for processing information, which may include one or more microprocessors, microcontrollers, application-specific-integrated circuits (ASICs), or the like, and which may include any suitable form of volatile or non-volatile memory for electronic information storage. Electro-active optics 206 includes any device that can change its electrical power in response to a control signal, including but not limited to liquid crystals, electro-wetting lenses, electro-mechanically actuated optics, or any other controllable optic known in the art. Preferably, electro-active optic 206 has an optical power that can be tuned continuously or nearly continuously to provide a range of suitable powers corresponding to distance, near, and intermediate vision ranges in response to accommodation demand.

Processor 204 includes any suitable hardware, software, and/or firmware for receiving signals from sensors 102 and 104 representative of electrical fields in the ciliary muscle and determining an accommodation demand based on the signals. Various techniques known in the signal processing art may be employed to improve processor efficiency and/or signal-to-noise ratio to improve reliability and speed of the calculation. For example, signals may be processed to determine RMS variations or to rectify the incoming signal. Integrating data over time and/or filtering in time and/or frequency, including the use of Fourier and wavelet transforms or recursive filters such as Kalman figures, may also be useful. Likewise, as noted above, the relationship between the electric field in the ciliary muscle and accommodation demand can be determined for particular patients or for a patient population to provide a control signal.

Electromyography provides a promising sensing approach for automatically focusing ("autofocus") electro-active ophthalmic lenses. One particular difficulty associated with previous attempts at producing such lenses is that it is difficult to find a reliable trigger to indicate the full range of possible accommodation demand, so as to detect both near and intermediate focus. Another difficulty is that the trigger must be sufficiently reliable to unambiguously discern whether the patient is actually accommodating. Both of these difficulties would need to be overcome to provide patients with a full range of accommodation equivalent to the eye's natural performance before presbyopia. Based on the demonstrated response in skeletal muscles, electromyography should have improved results in this regard relative to other detection techniques for accommodation demand.

Other patients, particularly those suffering from AMD, may have different functional vision requirements. In the case of AMD patients, for example, the patients may require a high degree of magnification (6-8 Diopters) to be able to perform near or intermediate vision tasks. In particular, the near image may be magnified to allow features of the image to be detected by parts of the retina that are not impaired by a scotoma. Conventional treatments use magnification devices that may be cumbersome and inconvenient to carry. At the same time, many of these patients are not able to perform near vision tasks without magnification devices, so that they do not have as much need for automatic switching for visual tasks. Other patients may have a lifestyle that does not involve tasks such as driving where automatic switching from near to distance vision may be critical. Depending on such patients' needs, it may be feasible for the patient to have a system that is manually switched from near to far vision.

Figure 3:
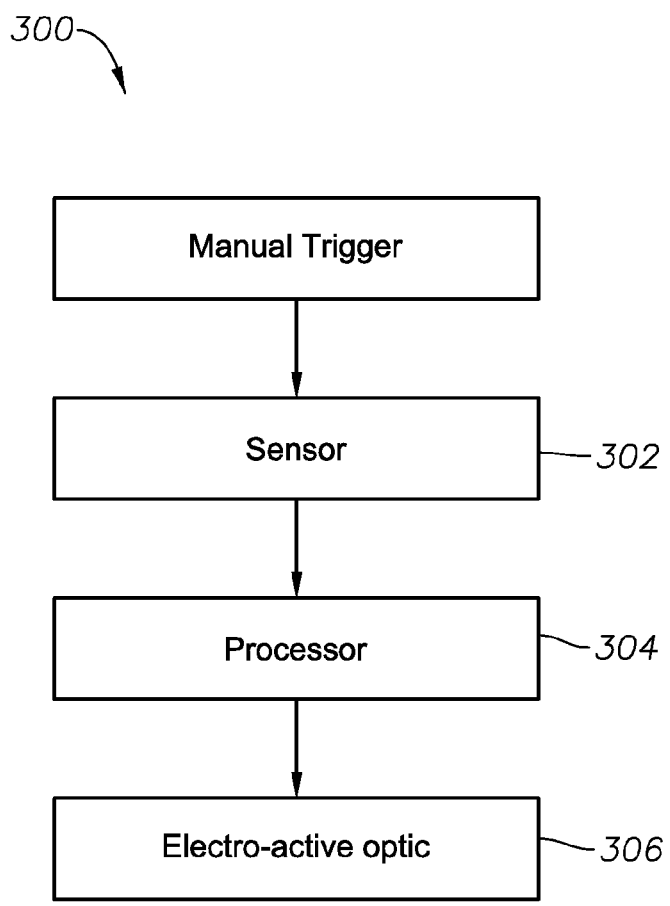
FIG. 3 illustrates a block diagram of an electro-active ophthalmic lens using a manual trigger, according to certain embodiments of the present disclosure.

FIG. 3 shows a block diagram of an electro-active ophthalmic lens 300 using a manual trigger. Sensors 302 may include any manner of detection device adapted to the manual trigger in question, while processor 304 and electro-active optic 306 are analogous to processor 204 and electro-active optic 206 described above as suitably adapted for the particular manual trigger. In one example of manual operation, sensors 302 may include a light level sensor used to detect an ambient light level. The trigger could be a particular blink pattern switching from distance vision to near or intermediate vision. In more complicated optical detection systems, a characteristic pattern of motion and/or heat signature of a hand or finger within the field of vision could be detected. Sensors 302 could be pressure sensors that detect pressure applied to the eye, such as a finger pressing on the sclera or a subdermal switch at another location that sends a signal to processor 304. Sensors 302 could also be audio sensors for detection of voice commands for activation.

Sensors 302 could also be electromagnetic sensors. For example, sensors 302 could detect input from a wireless remote that can provide binary or tunable control for the optical power of the electro-active element. Such a remote could include, for example, a hand-held device, a bracelet, a wristwatch, a key fob, or other suitable wireless communication remote. A magnetic trigger could also be used so that, for example, a magnetic ring or bracelet could be waved near sensors 302. An electroencephalography (EEG) signal could also be used to indicate brain activity characteristic of an intended switch.

Even for manual sensors, it may be advantageous to have some sort of automatic reversion to distance vision in order to relieve the patient from the need to switch back to distance vision under certain circumstances. For example, head position might be detected, so that when the patient looks up for a certain amount of time, the electro-active element reverts to distance vision. Likewise, there could be a certain time limit beyond which a patient must trigger near vision again. In another example, a remote control could periodically broadcast a signal, and if the signal is not detected, such as when the remote is not in close proximity or when it runs out of batteries, then the electro-active element could revert to distance vision. Alternatively, a remote control could continue broadcasting a signal, such as when a button is held down, so that the electro-active optic automatically reverts to distance vision when the signal is interrupted. These conditions under which the electro-optical element reverts to its original optical power may generally be referred to as "fail-safe conditions."

Those having ordinary skill in the art will appreciate that various changes can be made to the above embodiments without departing from the scope of the invention.

What is claimed is:

1. An electro-active ophthalmic lens, comprising:
   a plurality of electromyography sensors including at least one reference sensor, the plurality of electromyography sensors configured to detect an electric field in a ciliary muscle of the eye that is proportional to a force exerted by the ciliary muscle and to generate a sensor signal indicative of the electric field;
   a processor coupled to the electromyography sensor operable to receive the signal from the electromyography sensor and to determine, based on the sensor signal, an adjustment to optical power for an electro-active optical element and to generate a control signal for the electro-active optical element; and
   the electro-active optical element coupled to the processor operable to receive the control signal and to change an optical power of the electro-active optical element in response to the control signal.

2. The lens of claim 1, wherein the lens is an intraocular lens.

3. The lens of claim 1, wherein the lens is a contact lens.

4. The lens of claim 1, wherein the at least one reference sensor is operable to provide a reference potential.

5. The lens of claim 1, wherein the at least one sensor comprises an electrode in contact with the ciliary muscle.

6. The lens of claim 1, wherein the at least one sensor comprises a non-contact electromagnetic sensor.

* * * * *